United States Patent [19]
Nomura et al.

[11] Patent Number: 5,925,382
[45] Date of Patent: Jul. 20, 1999

[54] ANTIOXIDANT COMPOSITION AND METHOD FOR PRODUCTION THEREOF

[75] Inventors: Mitsuyoshi Nomura, Kyoto; Takao Ohta, Hirakata; Kenichi Koyama, Kameoka; Yoshikazu Matsuda, Kyoto, all of Japan

[73] Assignee: Japan Clinic Co., Ltd., Kyoto, Japan

[21] Appl. No.: 08/852,172

[22] Filed: May 7, 1997

[30] Foreign Application Priority Data

May 9, 1996 [JP] Japan ..................................... 8-115135
Apr. 30, 1997 [JP] Japan ..................................... 9-112328

[51] Int. Cl.$^6$ ..................................................... A61K 35/56
[52] U.S. Cl. ........................... 424/547; 424/520; 424/548
[58] Field of Search ..................................... 424/520, 547, 424/548

[56] References Cited

FOREIGN PATENT DOCUMENTS

| 61-010515 | 1/1986 | Japan . |
| 61-068420 | 4/1986 | Japan . |
| 61-139346 | 6/1986 | Japan . |
| 62-207223 | 9/1987 | Japan . |
| 62-257359 | 11/1987 | Japan . |
| 07102252 | 4/1995 | Japan . |

*Primary Examiner*—Jean C. Witz
*Attorney, Agent, or Firm*—Leydig, Voit & Mayer, Ltd.

[57] ABSTRACT

An antioxidant composition can be obtained efficiently at high yields by (a) adding ethanol to a hot water fraction of an oyster meat to a final concentration of not less than 40 (w/w) % to obtain a supernatant (step 1), (b) concentrating the obtained supernatant to a solid content of 30–45 (w/w) % (step 2), and (c) adding ethanol thereto to a final concentration of 55–70 (w/w) % to recover precipitates (step 3).

11 Claims, 1 Drawing Sheet

ANTIOXIDANT COMPOSITION AND METHOD FOR PRODUCTION THEREOF

TECHNICAL FIELD OF THE INVENTION

The present invention relates to an antioxidant composition obtained from hot water extract of oyster meat and a method for production thereof.

BACKGROUND OF THE INVENTION

Oxygen produces superoxide anion radical called active oxygen having a strong toxicity as a result of exposure to ultraviolet rays or radiation. It is converted to hydrogen peroxide or hydroxy radical and causes various oxidative disorders in human. It is considered that said mechanism causes various diseases inclusive of aging and oncogenesis.

Antioxidant enzymes such as superoxide dismutase (SOD) and antioxidant substances in the body have been increasingly recognized to have critical protective biological action against such oxidative disorders. In addition, antioxidant substances taken in as food have been attracting attention for their potential significant role in the prevention of oxidative disorders.

Incidentally, an oyster meat is also called milk in the sea because it contains large amounts of taurine, glycogen, protein and other useful substances.

SUMMARY OF THE INVENTION

As a result of the study and investigation of the components of oyster meat, it has now been found according to the present invention that a superior antioxidant composition contained in the oyster meat can be obtained at high purity by adjusting the alcohol concentration and solid content during alcohol fractionation.

Accordingly, the present invention provides the following.

(1) A method for producing an antioxidant composition, which comprises the steps of:
(a) adding ethanol to a hot water fraction of an oyster meat to a final concentration of not less than 40 (w/w) % to obtain a supernatant (step 1);
(b) concentrating the obtained supernatant to a solid content of 30–45 (w/w) % (step 2); and
(c) adding ethanol thereto to a final concentration of 55–70 (w/w) % to recover precipitates (step 3).
(2) The method of the above (1), comprising adjusting the supernatant to have a pH of 3 or below before proceeding to step (c).
(3) The method of the above (1) or (2), which satisfies at least one of the following requirements:
(i) a final concentration of ethanol of 40–50 (w/w) % in step 1,
(ii) a solid content of 35–40 (w/w) % in step 2, and
(iii) a final concentration of ethanol of about 60 (w/w) % in step 3.
(4) An antioxidant composition characterized by the following properties:
(i) containing substances having a molecular weight of 1000–5000
(ii) UV absorption spectrum (see FIG. 1) $\lambda_{max}$ (aqueous solution): 267.5 nm and 198 nm
(iii) ninhydrine reaction: positive
(iv) main component: low molecular weight peptide
(v) solubility: water soluble
(vi) color: dark brown (5) The antioxidant composition of the above (4), which is prepared according to a production method comprising the steps of:
(a) adding ethanol to a hot water fraction of an oyster meat to a final concentration of not less than 40 (w/w) % to obtain a supernatant (step 1);
(b) concentrating the obtained supernatant to a solid content of 30–45 (w/w) % (step 2); and
(c) adding ethanol thereto to a final concentration of 55–70 (w/w) % to recover precipitates (step 3).
(6) The antioxidant composition of the above (5), which is produced by the method further comprising adjusting the supernatant to have a pH of 3 or below before proceeding to step (c).
(7) The antioxidant composition of the above (5) or (6), which satisfies at least one of the following requirements:
(i) a final concentration of ethanol of 40–50 (w/w) % in step 1,
(ii) a solid content of 35–40 (w/w) % in step 2, and
(iii) a final concentration of ethanol of about 60 (w/w) % in step 3.

DETAILED DESCRIPTION OF THE INVENTION

Figure 1:
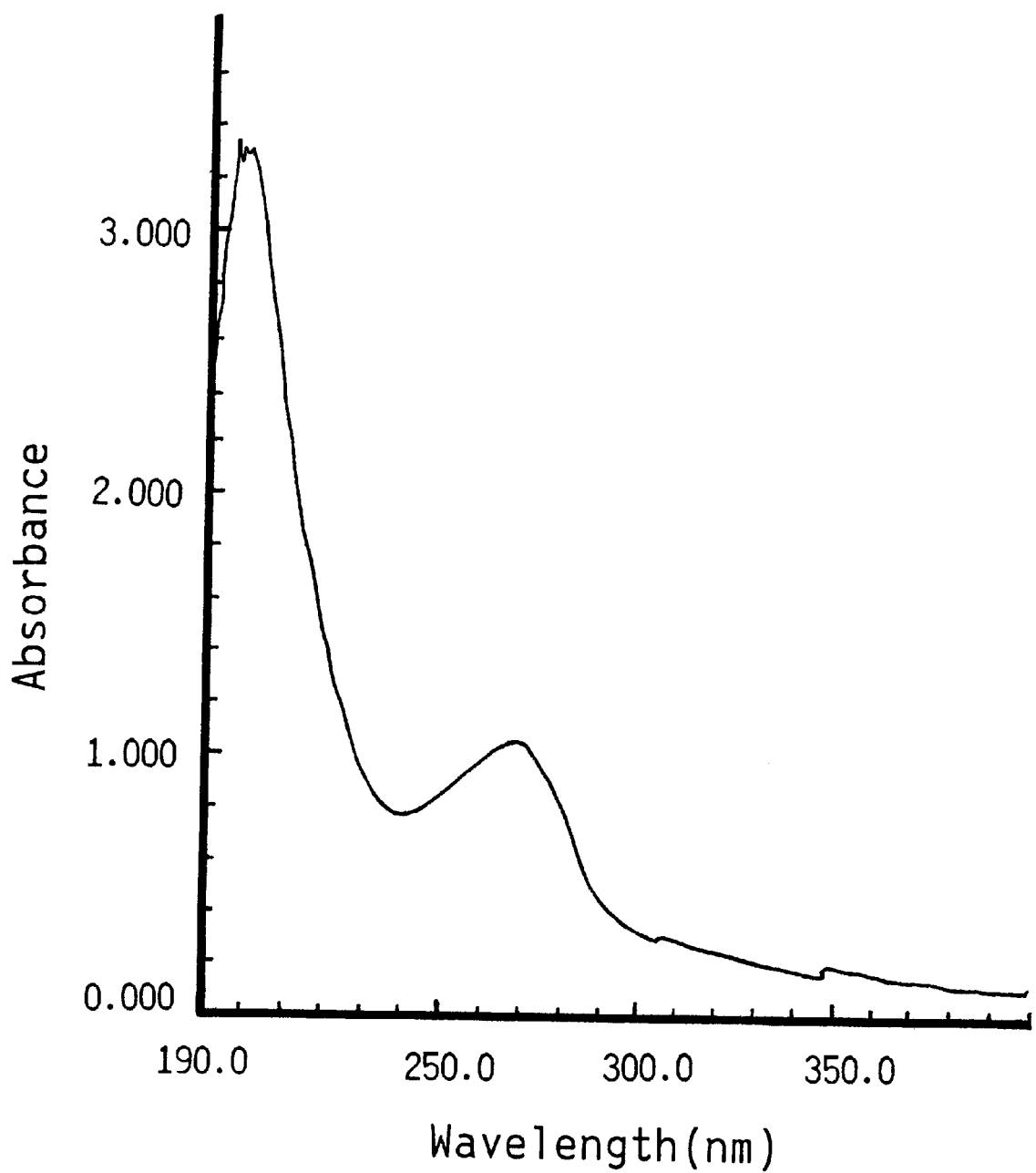
FIG. 1 shows a UV absorption spectrum of the antioxidant composition of the present invention.

In the present invention, a hot water fraction of an oyster meat is prepared, for example, by adding hot water to the oyster meat and removing precipitates to give a supernatant. The oyster meat to be the starting material in the present invention is not particularly limited in terms of shape as long as it retains the above-mentioned antioxidant activity, and may be raw, frozen or in a powder state prepared by drying and pulverizing the oyster meat. The temperature of the hot water to be used for hot water fractionation is generally 50–90° C., preferably about 70–80° C., and the time of extraction is generally 2 to 3 hours.

Inasmuch as said supernatant generally has a solid content of about 4–5 (w/w) %, it is preferable that the solid content be adjusted to 20–40 (w/w) % by concentration. A content outside this range fails to efficiently precipitate protein, glucide and the like.

Ethanol is known to cause precipitation by altering the polarity of a solvent, i.e., by varying the degree of hydrophobicity and hydrophilicity.

In step 1 of the present invention, the supernatant obtained by hot water fractionation is fractionated using ethanol at a final concentration of not less than 40 (w/w) %, preferably about 40–50 (w/w) %. When the final concentration of ethanol is less than 40 (w/w) %, high molecular weight protein and glucide which are unnecessary for the antioxidant activity cannot be removed sufficiently. What is more, the antioxidant activity of the obtained supernatant and that of the precipitates are almost the same. When the final concentration exceeds 50 (w/w) %, the effect of ethanol fractionation reaches saturation. The time of fractionation is generally 1–24 hours, preferably 5–12 hours.

In step 2 of the present invention, a different solid content results in a different intermolecular bonding force. A stronger or weaker intermolecular bonding results in difficult precipitation. When the solid content decreases, ionic strength becomes low to result in a lower intermolecular bonding force and less amounts of precipitates. In step 2 of the present invention, the supernatant obtained by the above-mentioned ethanol fractionation is concentrated to a solid content of 30–45 (w/w) %, preferably 35–40 (w/w) %. When the solid content is less than 30 (w/w) %, precipitates decrease in amount and so does antioxidant activity of the precipitates. When the solid content is greater than 45 (w/w) %, the precipitates include impurities unnecessary for the antioxidant activity and the specific antioxidant activity of the precipitates decreases. The supernatant is concentrated by, for example, heating concentration, membrane concentration, freezing concentration and the like, particularly preferably heating concentration under reduced pressure. The solid content can be determined as brix (sugar concentration) using a brix scale such as the manual refractometer manufactured by Atago Corp.

The above-mentioned concentrated liquid is adjusted to pH 3 or below, preferably about pH 3. The pH is generally adjusted by adding an acid such as hydrochloric acid and citric acid. Proteins and peptides readily precipitate at an isoelectric pH, and when the pH is higher than 3, the resulting precipitates decrease in amount.

After pH adjustment, ethanol is added to said solution so that the final concentration becomes 55–70 (w/w) %, preferably about 60 (w/w) %, and the mixture is centrifuged to recover precipitates. Said precipitates contain an antioxidant composition at a high concentration and exhibits antioxidant activity. When the final concentration of ethanol is less than 55 (w/w) %, the yield of the antioxidant composition becomes low, barely making difference in the antioxidant activity between the obtained precipitates and the supernatant. When it is higher than 70 (w/w) %, the precipitates increase in amount, but so do unnecessary contaminants, and the specific antioxidant activity becomes poor.

The antioxidant composition thus obtained has the following properties besides its antioxidant activity:

(i) containing substances having a molecular weight of 1000–5000

(ii) UV absorption spectrum (see FIG. 1) $\lambda_{max}$ (aqueous solution): 267.5 nm, 198 nm (iii) ninhydrine reaction: positive (iv) main component: low molecular weight peptide (v) solubility: water soluble (vi) color: dark brown The above-mentioned properties are confirmed by known methods. Specifically, the molecular weight is postulated based on the behavior of presence or absence of precipitate formation when subjected to alcohol fractionation. The UV absorption spectrum can be determined using an absorptiometer conventionally used. Solubility in water and color are observed according to the method defined in Japanese Pharmacopoeia. The main component can be determined by color reaction specific to each component, qualitative reaction or quantitative reaction conventionally used. The ninhydrine reaction permits confirmation of protein, polypeptide, amino acid and the like, and the presence of peptide can be confirmed by high performance liquid chromatography.

The present invention is described in more detail by way of Examples, which should not be construed as limiting the invention.

EXAMPLE 1

Water (50 g) was added to frozen raw oyster (50 g), and the mixture was heated at 80–90° C. for 2–3 hours for hot water extraction and centrifuged at 1500 rpm (Hitachi, Ltd.) for 10 minutes. The resulting supernatant was concentrated by heating to a solid content of 20–40 (w/w) %. Ethanol was added to the obtained concentration liquid to the final concentration of 40 (w/w) %, and after leaving for 12 hours, the mixture was centrifuged at 3000 rpm (Hitachi, Ltd.) for 10 minutes to recover a supernatant (step 1). The supernatant was concentrated by heating under reduced pressure at 50° C. using a rotary evaporator to a solid content of 37 (w/w) % (step 2). 0.1 M Hydrochloric acid was added to the obtained supernatant to adjust its pH to 3. Ethanol was added to said solution, which underwent adjustment of solid content and pH, to a final concentration of 60 (w/w) %. After leaving for 12 hours, the mixture was centrifuged at 3000 rpm (Hitachi, Ltd.) for 10 minutes to recover the resulting precipitates as an antioxidant composition (step 3). The obtained precipitates were examined for properties as in the following.

(i) In view of the fact that the precipitates were obtained by subjecting a supernatant obtained by 40 (w/w) % alcohol fractionation of a hot water extract of oyster meat, to 60 (w/w) % alcohol fractionation, it is postulated that the fraction contained large amounts of substances having a molecular weight of 1000–5000.

(ii) A small amount of the obtained precipitates was dissolved in water and the UV absorption spectrum thereof was determined using a UV-2400 PC (SHIMADZU CORPORATION). The results are shown in FIG. 1. As a result, the absorption peaks were found at 267.5 nm and 198 nm.

(iii) A small amount of the obtained precipitates was dissolved in water and a ninhydrine reagent (0.2 g ninhydrine dissolved in 10 ml water) was added. Heating and cooling thereof resulted in blue purple (positive) color development.

(iv) High performance liquid chromatography under the following conditions led to the detection of a peak, thus confirming the presence of peptides.

conditions:

column: Shodex Asahipak ODP-50 6E eluate:

0.1 M sodium perchlorate+0.1% sodium phosphate buffer (pH 2)/acetonitrile=90/10

0.1 M sodium perchlorate+0.1% sodium phosphate buffer (pH 2)/acetonitrile=60/40 linear gradient for 60 minutes flow rate: 1.0 ml/min detector: SPD-10A (SHIMADZU CORPORATION)

column temperature: 30° C.

(v) Solubility in water was determined at normal temperature and the color was confirmed on a white paper. As a result, the precipitate was found to be water soluble and the color developed was dark brown.

The foregoing results matched with the properties of the above-mentioned antioxidant composition.

EXAMPLE 2

The same steps as in Example 1 were repeated except that the solid content was adjusted to 45 (w/w) % in step 2, whereby precipitates were obtained. The obtained precipitates had the same properties with those of the above-mentioned antioxidant composition.

EXAMPLE 3

The same steps as in Example 1 were repeated except that ethanol was added to the solution after adjustment of solid content and pH, to a final concentration of 70 (w/w) % in step 3, whereby precipitates were obtained. The obtained precipitates had the same properties with those of the above-mentioned antioxidant composition.

COMPARATIVE EXAMPLE 1

The same steps as in Example 1 were repeated except that ethanol was not added to the hot water fractionation supernatant of oyster meat in step 1, whereby precipitates were obtained.

COMPARATIVE EXAMPLE 2

The same steps as in Example 1 were repeated except that the solid content was adjusted to 18.5 (w/w) % in step 2, whereby precipitates were obtained.

COMPARATIVE EXAMPLE 3

The same steps as in Example 1 were repeated except that ethanol was added to the solution after adjustment of solid content and pH, to a final concentration of 80 (w/w) % in step 3, whereby precipitates were obtained.

EXPERIMENTAL EXAMPLE 1

Determination of antioxidant activity

The amounts of the precipitates obtained per 100 g of the oyster meat hot water extracts obtained in Examples 1 to 3 and Comparative Examples 1 to 3, and the antioxidant activity of the precipitates were determined. In this Experimental Example, the antioxidant activity was determined by measuring the erased activity of active oxygen (superoxide anion), which determination was performed according to the ESR spin trap method. The ESR spin trap method includes reacting an extremely unstable radical with a trapping agent to detect comparatively stable radical. In this Experimental Example, an active oxygen was produced in a xanthine-xanthine oxidase system and determined using DMPO (5,5-dimethyl-1-pyrrollen-1-oxide) as a spin trapping agent. The amount of sample necessary for erasing the produced active oxygen by 50% (i.e. $IC_{50}$) was taken as an erased activity of the active oxygen, namely, antioxidant activity. A smaller $IC_{50}$ means stronger antioxidant activity. The results are shown in Table 1.

TABLE 1

| | precipitates (g) | antioxidant activity ($IC_{50}$) (μg) |
| --- | --- | --- |
| Example 1 | 1.5 | 0.035 |
| Example 2 | 1.5 | 0.030 |
| Example 3 | 1.6 | 0.041 |
| Comparative Example 1 | 56.2 | 0.579 |
| Comparative Example 2 | 1.9 | 0.066 |
| Comparative Example 3 | 2.5 | 0.090 |

According to the present invention, a highly pure antioxidant composition can be obtained from a hot water extract of an oyster meat with high efficiency at high yields.

This application is based on application No. 115135/1996 filed in Japan, the content of which is incorporated hereinto by reference.

What is claimed is:

1. A method for producing an antioxidant composition, which comprises the steps of:
   (a) adding ethanol to a hot water extract of an oyster meat to a final concentration of not less than 40 (w/w) % of ethanol to obtain a supernatant;
   (b) concentrating the obtained supernatant to a solid content of 30–45 (w/w) % of solids; and
   (c) adding ethanol thereto to a final concentration of 55–70 (w/w) % of ethanol to recover precipitates containing the antioxidant composition.

2. The method of claim 1, comprising adjusting the supernatant to have a pH of 3 or below before proceeding to step (c).

3. The method of claim 1 or claim 2, which satisfies at least one of the following requirements:
   (i) a final concentration of ethanol of 40–50 (w/w) % in step (a),
   (ii) a solid content of 35–40 (w/w) % in step (b), or
   (iii) a final concentration of ethanol of about 60 (w/w) % in step (c).

4. An antioxidant composition characterized by the following properties:
   (i) containing substances having a molecular weight of 1000–5000
   (ii) UV absorption spectrum (see FIG. 1) $\lambda_{max}$ (aqueous solution): 267.5 nm and 198 nm
   (iii) ninhydrine reaction: positive
   (iv) main component: low molecular weight peptide
   (v) solubility: water soluble
   (vi) color: dark brown which is prepared according to a method comprising the steps of:
      (a) adding ethanol to a hot water extract of an oyster meat to a final concentration of not less than 40 (w/w) % of ethanol to obtain a supernatant;
      (b) concentrating the obtained supernatant to a solid content of 30–45% (w/w) % of solids; and
      (c) adding ethanol thereto to a final concentration of 55–70 (w/w) % of ethanol to recover precipitates containing the antioxidant composition.

5. The antioxidant composition of claim 4, which is produced by the method further comprising adjusting the supernatant to have a pH of 3 or below before proceeding to step (c).

6. The antioxidant composition of claim 4, which satisfies at least one of the following requirements:
   (i) a final concentration of ethanol of 40–50 (w/w) % in step (a),
   (ii) a solid content of 35–40 (w/w) % in step (b), or
   (iii) a final concentration of ethanol of about 60 (w/w) % in step (c).

7. The antioxidant composition of claim 5, which satisfies at least one of the following requirements:
   (i) a final concentration of ethanol of 40–50 (w/w) % in step (a),
   (ii) a solid content of 35–40 (w/w) % in step (b), or
   (iii) a final concentration of ethanol of about 60 (w/w) % in step (c).

8. A method for inhibiting oxidation comprising contacting a substrate with the antioxidant composition characterized by the following properties:
   (i) containing substances having a molecular weight of 1000–5000
   (ii) UV absorption spectrum (see FIG. 1) $\lambda_{max}$ (aqueous solution): 267.5 nm and 198 nm
   (iii) ninhydrine reaction: positive
   (iv) main component: low molecular weight peptide
   (v) solubility: water soluble
   (vi) color: dark brown which is prepared according to a method comprising the steps of:

(a) adding ethanol to a hot water extract of an oyster meat to a final concentration of not less than 40 (w/w) % of ethanol to obtain a supernatant;
(b) concentrating the obtained supernatant to a solid content of 30–45% (w/w) % of solids; and
(c) adding ethanol thereto to a final concentration of 55–70 (w/w) % of ethanol to recover precipitates containing the antioxidant composition.

9. The method of claim 8, wherein said antioxidant composition is produced by the method further comprising adjusting the supernatant to have a pH of 3 or below before proceeding to step (c).

10. The method of claim 8, wherein said antioxidant composition satisfies at least one of the following requirements:
(i) a final concentration of ethanol of 40–50 (w/w) % in step (a),
(ii) a solid content of 35–40 (w/w) % in step (b), or
(iii) a final concentration of ethanol of about 60 (w/w) % in step (c).

11. The method of claim 9, wherein said antioxidant composition satisfies at least one of the following requirements:
(i) a final concentration of ethanol of 40–50 (w/w) % in step (a),
(ii) a solid content of 35–40 (w/w) % in step (b), or
(iii) a final concentration of ethanol of about 60 (w/w) % in step (c).

* * * * *